United States Patent [19]

Ciambarella et al.

[11] Patent Number: 4,487,201
[45] Date of Patent: Dec. 11, 1984

[54] ORTHOPEDIC BACK SUPPORT FOR AN AUTOMOBILE

[76] Inventors: Ernest Ciambarella, 3511 Constitution St., Cincinnati, Ohio 45211; Jeffrey L. Quirk, 1302 Epworth Ave., Dayton, Ohio 45410

[21] Appl. No.: 443,062

[22] Filed: Nov. 19, 1982

[51] Int. Cl.³ ............................................. A61F 13/00
[52] U.S. Cl. .................................... 128/134; 297/484
[58] Field of Search ............... 128/134, 133, DIG. 15, 128/78, 75; 297/484, 485, 464, 465, 466-469, 482

[56] References Cited

U.S. PATENT DOCUMENTS

| | | | |
|---|---|---|---|
| 2,288,692 | 7/1942 | Fearson | 155/189 |
| 2,576,867 | 11/1951 | Wilson, Jr. | 297/484 |
| 2,726,714 | 12/1955 | McAndrews | 128/134 |
| 3,160,143 | 12/1964 | Gray | 119/96 |
| 3,167,068 | 1/1965 | Carr | 128/75 |
| 3,321,247 | 5/1967 | Dillender | 297/484 |
| 3,367,715 | 2/1968 | Curran | 297/484 |
| 3,834,758 | 9/1974 | Soule | 297/484 |
| 4,022,197 | 5/1977 | Castiglina | 128/101 |
| 4,030,489 | 6/1977 | Buckner | 128/75 |
| 4,205,670 | 6/1980 | Owens | 128/134 |

FOREIGN PATENT DOCUMENTS 2252168  5/1974  Fed. Rep. of Germany ...... 297/484

Primary Examiner—John D. Yasko
Attorney, Agent, or Firm—Kinney and Schenk

[57] ABSTRACT

An orthopedic back support for an automobile includes a flexible suspension band designed to wrap around persons of varying size. The suspension band is supported in adjacent relationship to a substantially vertical backrest of the automobile seat by straps which overlap the top of that automobile seat backrest. The suspension belt partially supports the weight of the upper torso of an occupant in the automobile, removing the supported weight from the lower back portion of the spine.

13 Claims, 7 Drawing Figures

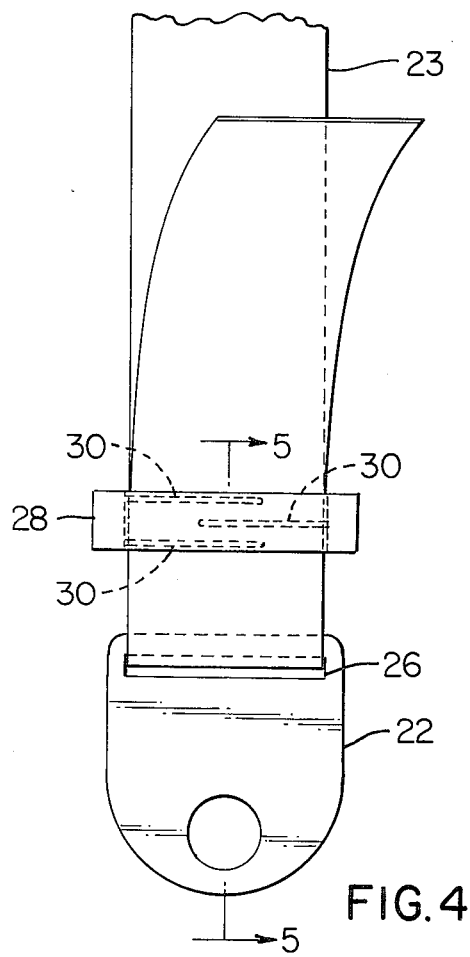
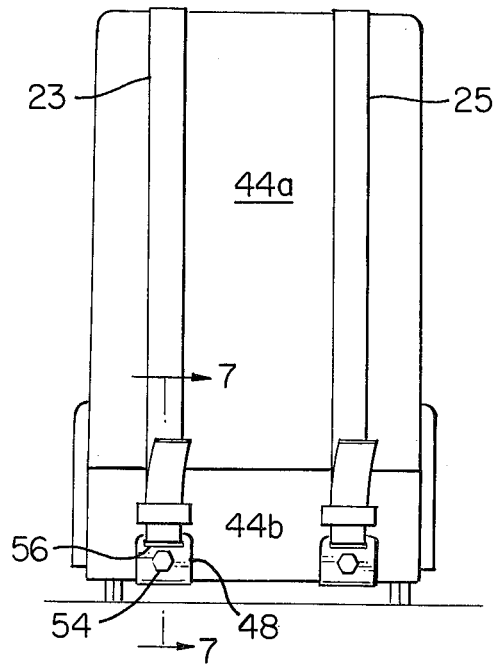
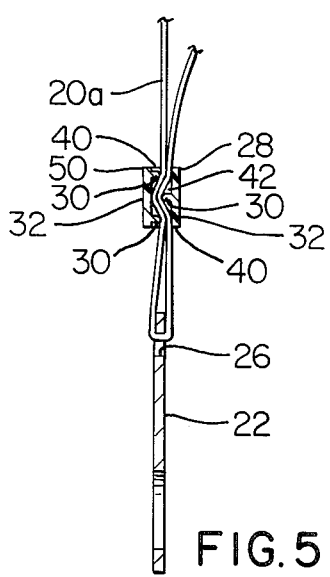
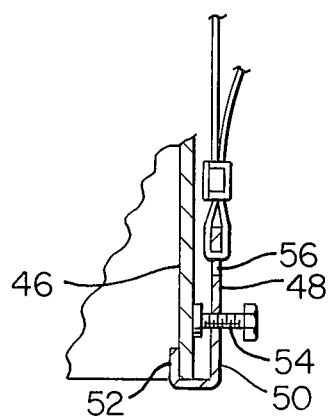
FIG. 4
FIG. 6
FIG. 5
FIG. 7

ORTHOPEDIC BACK SUPPORT FOR AN AUTOMOBILE

BACKGROUND OF THE INVENTION

It is an unfortunate fact that many people suffer from pain and discomfort of the lower back. This pain and discomfort is aggravated by extended traveling in an automobile. In the past, lower back pain sufferers have been relegated to enduring substantial discomfort during extended automobile rides or extended periods of sitting in one position. Not only do such people undergo pain during time period of the automobile trip or sitting, they also frequently suffer from the resulting pain for many hours after the automobile trip or extended periods of sitting has ended.

Applicant has found that much of this pain may be alleviated by properly supporting the back while riding or sitting for extended periods of time. Specifically, it has been found that removing body weight from the lower portion of the spine by supporting the weight of the upper torso during the automobile trip or extended sitting effectively precludes the occurrence of lower back pain which results from traveling in an automobile or sitting for an extended period.

It is thus an object of the present invention to provide an orthopedic back support for the seat of an automobile or any chair or seat which relieves lower back pain of the type that occurs in many people from riding in an automobile or sitting for an extended period.

It is a further object of the present invention to partially support the weight of an automobile occupant at a location above the lower back portion.

It is another object of the present invention to provide an orthopedic seat support that will wrap around persons of different sizes.

It is yet another object of the present invention to provide an orthopedic seat support which is secured to the seat of an automobile or any seat.

SUMMARY OF THE INVENTION

In accordance with the present invention, an automobile with a seat therein is provided with an orthopedic back support which serves to remove weight from the lower spine of an automobile occupant or person in the sitting position when that occupant or person is sitting in the automobile seat or other seat. A suspension band is disposed adjacent to the vertical back seat support in the automobile or chair and spaced from the horizontal seat support by a predetermined distance. The suspension band has two end portions which are selectively engageable with each other to completely circumscribe the upper torso of the occupant sitting in the automobile seat or chair. The suspension band is adjustable to fit about persons of varying size. Means are also provided for vertically supporting the suspension band against downward gravity biased movement and to partially support the weight of an occupant sitting in the seat with the suspension band circumscribing the upper torso.

In accordance with a further aspect of the invention, the spacing of the suspension band from the horizontal seat support is adjustable.

In a more specific aspect of the invention, the vertical supporting means includes a strap secured to the suspension band.

In a still further feature of the invention, the strap is connected to the seat and extends over the top of the vertical back support of the automobile seat or chair.

According to a further aspect of the invention, a mounting plate is attached to the end of the strap and the mounting plate is adapted for securement to the seat.

In a further aspect of the invention, the mounting plate has a slot and the strap is inserted through the slot and folded back on itself.

In a further aspect of the invention, a clip for selectively engaging the strap and frictionally engaging the overlaid portions thereof is provided to prevent relative movement between the various portions of the strap.

According to a further aspect of the invention, the mounting plate includes a U-shaped portion which is adapted to engage a portion of the seat.

A still further aspect of the invention includes a securement member threadably received by the mounting plate. The securement member is adapted to engage a portion of the seat adjacent to the portion engaged by the U-shaped portion of the mounting plate when the mounting plate is engaged in the seat.

BRIEF DESCRIPTION OF THE DRAWINGS

Other objects and advantages of the invention will become apparent upon reading the following detailed description and upon reference to the drawings, in which:

FIG. 4 is a fragmentary view of an end of one of the straps of the orthopedic supporting apparatus of FIGS. 1-3 showing an attachment plate through which the strap is inserted.

FIG. 5 is a sectional view through the strap of FIG. 4 showing the strap in overlapping relation to itself with the overlapped portion secured by an adjustment clip.

FIG. 6 is a rear elevational view of an automobile seat similar to FIG. 3 but showing a modified attachment plate and method of securing the straps to the seat.

FIG. 7 is a sectional view taken along line 77 in FIG. 6 showing the modified attachment plate in engaging relationship to the rear of the seat.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION ON PREFERRED EMBODIMENT

Figure 1:
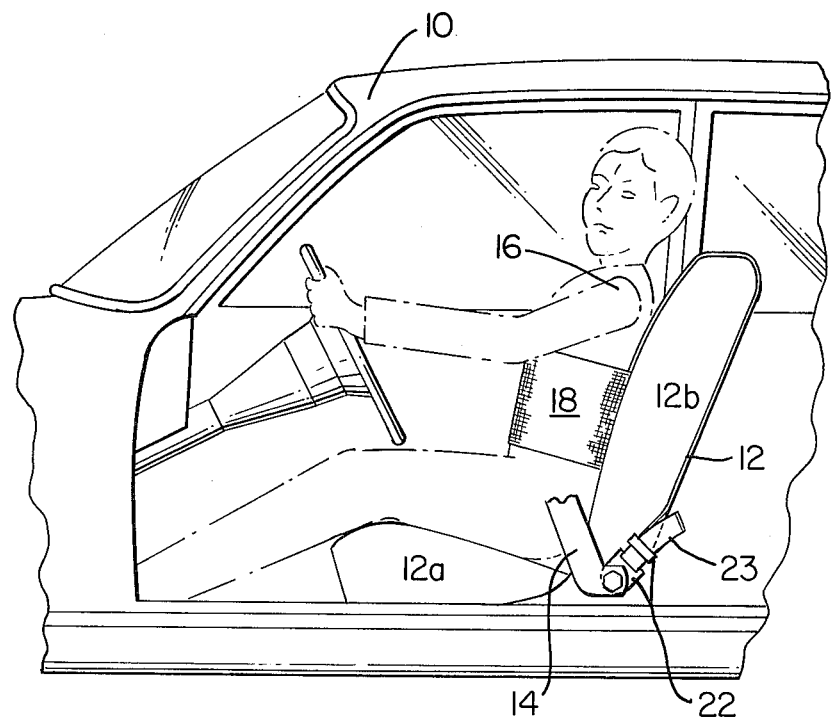
FIG. 1 is a fragmentary side elevational view of an automobile with the side door removed depicting a person utilizing an orthopedic supporting apparatus formed in accordance with the present invention.

Referring now to the drawings and to FIG. 1 in particular, a portion of an automobile 10 is shown with its side door removed to illustrate the passenger compartment thereof. The automobile 10, as is typical, has a pair of seats for seating occupants, including a driver and several passengers. However, only the front seat 12 of the pair of seats is shown in FIG. 1. The front seat 12 includes a generally horizontal support 12a which is intended to support the majority of the automobile occupant's 16 weight. This generally horizontal support 12a is joined by a substantially vertical back support 12b which is intended primarily as a back support for the occupant 16. As is conventional, a seat belt 14 is affixed to the seat 12 for wrapping around the occupant 16 seated in the seat 12 and retaining that occupant 16 in the seat 12 in the event of sudden deacceleration of the automobile 10.

A suspension band 18 is shown in FIG. 1 circumferentially fitted about the upper torso of the occupant 16 seated in the seat 12. This suspension band 18 is shown more clearly in FIG. 2 where it is seen that the suspension band 18 is a continuous flexible member with two free ends 18a and 18b. The suspension band 18 is secured to the seat 12 through the agency of a strap 20 which is sewn or otherwise fastened to a central portion of the suspension belt 18, intermediate the suspension belt's free ends 18a and 18b.

The suspension belt 18 has complementary hook and loop fasteners 21, 22 proximal to the free ends 18a and 18b, the free ends 18a and 18b being adapted for overlapping engagement with each other. Hook and loop fasteners of this type (sold under the Trademark Velcro) will support very substantial sheer forces but relatively small tensile forces. Thus, when an occupant 16 securely wraps the flexible suspension band 18 about his/her upper torso and engages the hook and loop fasteners 19 and 21, the torso tends to expand the wrap suspension band 18 radially outward, exerting sheer forces on the overlapped and engaged hook and loop fasteners 19, 21. As indicated above, these fasteners 19, 21 will support very substantial forces in this direction. On the other hand, when the free ends 18a and 18b are subjected to tensile forces as, for example, when the occupant 16 grasps the outermost of the free ends 18a and pulls it away from his/her body, the hook and loop type fasteners release quite readily. Hook and loop fasteners of this type are well known in the art and no further description thereof is deemed necessary.

Figure 2:
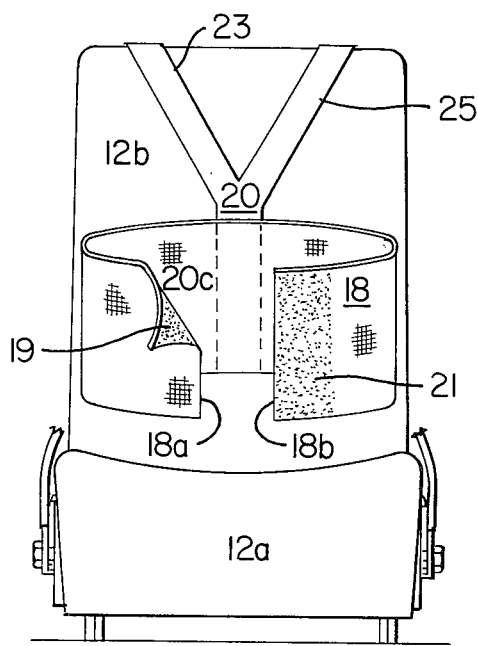
FIG. 2 is a front elevational view of the automobile seat of FIG. 1 showing the orthopedic supporting apparatus and its relationship to the seat in greater detail.

As shown in FIG. 2, the strap 20 is joined by two other straps 23 and 25 to form a generally Y-shaped configuration with the two other straps 23 and 25 joining the strap 20 proximal to suspension band 18. The straps 23 and 25 diverge as they extend away from the strap 20 and wrap about the top of the substantially vertical seat support 12b.

Figure 3:
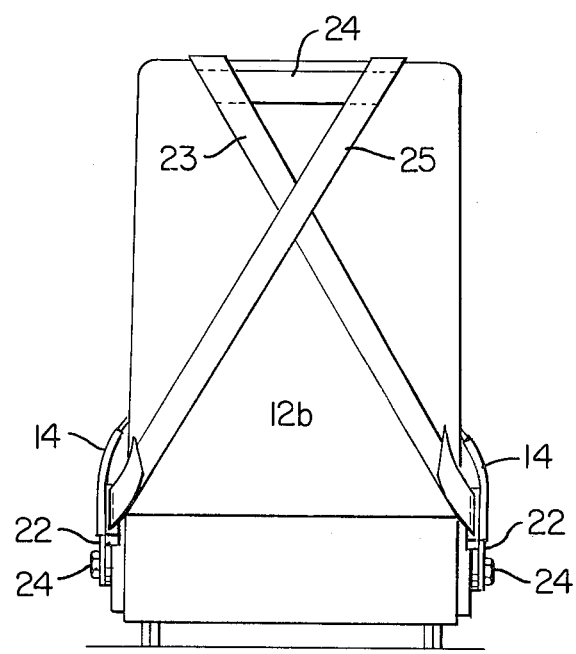
FIG. 3 is a rear elevational view of the automobile seat of FIGS. 1 and 2 illustrating one manner of securing the straps of the orthopedic supporting apparatus.

On the back of the seat, as depicted in FIG. 3, it is seen that the straps 23 and 25 criss-cross each other and extend to the bottom of the seat 12. Each of the straps 23 and 25 are secured to the mounting or attachment plate 22, which attachment plates are designed for securement to the seat 12. These attachment plates 22 are shown on the sides of the seat 12 in FIG. 1. The attachment or securement plates 22 are, in turn, secured to a seat belt fixture 24 through the agency of bolts 27 which extend through apertures 22a in the mounting plates 22. A rigid reinforcing member 24 extends between the strap 23 and 25 above the criss-cross of those two straps to prevent these two straps from sliding toward each other as might otherwise result in the criss-cross design when the straps 23 and 25 are put under tension.

The end portions of the straps 23 and 25 and their relationship to the mounting or attachment plate 22 is depicted in greater detail in FIG. 4. Since the straps 23 and 25 are identical in their relationship to the mounting or attachment plates 22, only the end of strap 23 will be shown in detail in FIG. 4, it being understood that the strap 25 would be identical in its relationship to mounting or attachment plate 22. It is seen from FIG. 4 that the attachment plate 22 has an elongated slot orifice 26 through which the strap 23 may be inserted. Once inserted through the slot 26, the strap 23 is folded back in overlapping relationship with itself. An adjustment clip 28 securely holds the overlapping portions of the strap 23 in tight frictional engagement with each other to prevent the free end of that strap 23 from sliding back through the slot orifice 26.

The cross sectional view of FIG. 5 shows the strap 23 held in overlapping relationship with itself by an adjustment clip 28. The strap 23 extends from the top of the vertical seat support 12a through the adjusting clip 28 and orifice slot 26 of the mounting plate 22 and back through the adjusting clip 28. A plurality of ribs 30 extend from opposite sidewalls 32 of the adjusting clip 28 toward a tortuous pathway 42 extending between the end walls 40 of that adjustment clip 28. Strap 23 may be passed through this tortuous pathway 42 only by a flexing. Thus, so long as it is able to flex, the strap 23 may be passed through this tortuous pathway 42. However, when the strap 20a is under tension, it resists flexing and is urged toward a straight allignment. Bringing the strap 23 into a straight alignment pushes the overlapping portions of the strap 23 into the compressive engagement with each other and with the ribs 30. The resulting compressive forces prevent the overlapped components from sliding relative to each other and prevent the free end of the strap 23 from sliding back through the orifice slot 26 of the mounting plate 22. Adjustment clips of this type are well known in the art and are commercially available.

A modified method of securing the straps 23 and 25 is depicted in FIG. 6 in which the straps 23 and 25 continue straight down from the top of the vertical seat support 12b to the bottom rear edge of the adjoined horizontal seat support 12a. The rear of the horizontal seat support 12a has a metal plate 46 which provides an engagement surface for a modified attachment plate 48 depicted in FIGS. 6 and 7. This modified attachment plate 48 engages the bottom of the metal wall 46 with a U-shaped portion 50 on its bottom portion. The U-shaped portion 50 has a vertical sidewall 52 which is positioned against the inside wall of the metal plate 46 and a bottom wall 54 which is in engagement with the bottom of the metal plate 46. The sidewall 52 of the U-shaped portion 50 is held into engagement with the inside surface of metal plate 46 by a pressure member 56, the pressure member 56 being threadably received by the attachment plate for pressure engagement with the outside surface of the metal plate 46.

The mounting plate 48, like the previously described mounting plate 22, has a slot orifice 56 through which the straps 23 and 25 in the FIGS. 6 and 7 arrangement may be inserted and arranged in overlapping relationship upon themselves. Similarly, an adjusting clip 28 secures the straps 23 or 25 and their overlapping relationship as previously described.

In use, the occupant 16 would initially position himself against both the horizontal and vertical seat supports 12a and 12b as is conventional. He/she would thereafter raise his/her upper torso approximately three to four inches off the horizontal seat support. The raising of the occupant's upper torso may be achieved by that occupant pressing against the floor of the automobile 10 with his/her legs. Once the upper torso is elevated approximately three or four inches, the suspension belt 18 is wrapped around that occupant's upper torso with the free ends 21 and 22 overlapped to engage each other. The occupant then relieves the pressure on his/her legs and slides back toward the substantially horizontal seat support 12b. However, a portion of the upper torso's weight will now be supported by the suspension band 18. Support of the upper body weight in this manner relieves substantial stress on the lower back of the occupant. Thus, occupants with lower back problems may ride in the automobile for many hours with this suspension belt 18 without suffering the pain and discomfort previously associated with rides of long duration.

Thus it is apparent that there has been provided, in accordance with the invention, an orthopedic back support that fully satisfies the objects, aims and advantages set forth above. While the invention has been described in conjunction with a specific embodiment thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. In combination with an automobile having a seat therein, said seat having a substantially horizontal support and a substantially vertical back support, an apparatus for partially transferring body weight from the lower lumbo-sacral and pelvic regions by supporting the weight of a person's lower thoracic region in said automobile, said apparatus comprising:
    a flexible suspension band, said suspension band being disposed adjacent to said vertical back support, said suspension band being spaced from said horizontal support, said suspension band having two end portions, said end portions being selectively engageable with each other to completely circumscribe said lower thoracic region of a person sitting in said seat, said suspension band being adjustable to fit about persons of varying size; and
    means for vertically supporting from above said suspension band against downward gravity biased movement, said means partially supporting the weight of said person sitting in said seat with said suspension band circumscribing said lower thoracic region of said person, said apparatus othopedically properly supporting said lower lumbo-sacral and pelvic regions of said person.

2. A combination as recited in claim 1 wherein the spacing of said suspension band from the horizontal support is adjustable.

3. A combination is recited in claim 2 wherein said vertically supporting means includes the straps secured to said suspension band.

4. A combination is recited in claim 3 wherein said strap is connected to said seat.

5. A combination is recited in claim 4 wherein said strap extends over the top of said substantially back vertical back support of said seat.

6. In combination with an automobile having a seat therein, said seat having a substantially horizontal support and a substantially vertical back support, an orthopedic back support for partially transferring body weight from the lower portion of the spine by supporting the weight of a person's upper torso in said automobile, said orthopedic back support comprising:
    a flexible suspension band, said suspension band being disposed adjacent to said vertical back support, said suspension band being adjustably spaced from said horziontal support, said suspension band having two end portions, said end portions being selectively engageable with each other to completely circumscribe the upper torso of said person sitting in said seat, said suspension band being adjustable to fit varying size persons; and
    means for vertically supporting said suspension band against downward gravity biased movement, said means partially supporting the weight of a person sitting in said seat with said suspension band circumscribing said upper torso of said person, said back support orthopedically properly supporting said back of said person, said means for vertically supporting said suspension band further comprising:
    at least one strap, said strap extending over the top of said substantially vertical back support of said seat, said strap being operatively secured to said suspension band and said seat.

7. A combination is recited in claim 6 further comprising:
    a mounting plate attached to the end of said strap, said mounting plate being adapted for securement to said seat.

8. A combination is recited in claim 7 wherein said mounting plate has a slot, said strap being inserted through said slot and folded back on said strap.

9. A combination is recited in claim 8 further comprising;
    a clip for selectively engaging said strap and for selectively engaging said strap and for frictionally engaging said overlayed portions of said strap to prevent relative movement therebetween.

10. A combination as recited in claim 9 wherein said mounting plate includes a U-shaped portion adapted to engage a portion of the seat.

11. A combination as recited in claim 10 further including a securement member threadability received by said mounting plate, said securement member being adapted to engage a portion of the seat adjacent to the portion engaged by U-shaped portion of the mounting plate when the mounting plate is engaging the seat.

12. An apparatus for partially transferring body weight from the lower portion of the spine by supporting the weight of a persons upper torso, said apparatus comprising:
    a horizontal support member;
    a vertical support member;
    a flexible suspension band, said suspension band being disposed adjacent to said vertical back support, said suspension band being adjustably spaced from said horizontal support, said suspension band having two end portions, said end portions being selectively engageable with each other to completely circumscribe said upper torso of said person sitting on said substantially horizontal support member, said suspension band being adjustable to fit about persons of varying size; and
    means for vertically supporting said suspension band against downward gravity biased movement, said means partially supporting the weight of a person sitting on said horizontal support with said suspension band circumscribing said upper torso of said person, said back support orthopedically properly supporting said back of said person, said means for vertically supporting said suspension band further comprising:

at least one strap, said strap extending over the top of said substantially vertical back support member, said strap being operatively secured to said suspension band and to at least one of said vertical support member and said horizontal support member.

13. A method for partially transferring body weight from the lower portion of the spine by supporting the weight of a persons upper torso when said person is seated on a horizontal support, said method comprising:

initially positioning a person against both the horizontal and vertical support members;

raising the person's upper torso approximately 3-4 inches off the horizontal support, said raising being accomplished by said person pressing against the floor with their legs;

wrapping a suspension band about said persons upper torso;

connecting the free ends of said suspension belt;

relieving the pressure on said persons legs;

allowing said person to slide back toward said substantially horizontal support member;

supporting said person's upper torso by said suspension band, said suspension band being operatively connected to at least one strap, said strap extending over the top of said vertical support member, said strap being operatively connected at least one of said vertical support member and said horizontal support member.

* * * * *